United States Patent [19]

Boisson et al.

[11] Patent Number: 4,568,725

[45] Date of Patent: Feb. 4, 1986

[54] PRODUCTS BASED ON POLYMERS OR COPOLYMERS SUBSTITUTED BY GROUPS HAVING SELECTIVE AFFINITY TOWARDS PRODUCTS INVOLVED IN BLOOD PLASMA COAGULATION AND PROCESS FOR PREPARING SAME

[75] Inventors: Catherine Boisson, Paris; Danielle Gulino, Neuilly-Plaisance; Jacqueline Jozefonvicz; Marcel Jozefonvicz, both of Lamorlaye, all of France

[73] Assignee: Commissariat a l'Energie Atomique, Paris, France

[21] Appl. No.: 622,878

[22] Filed: Jun. 21, 1984

[30] Foreign Application Priority Data

Jun. 29, 1983 [FR] France ............................. 83 10773

[51] Int. Cl.$^4$ ............................................. C08F 8/30
[52] U.S. Cl. ............................. 525/330.5; 525/331.5; 525/333.1; 525/333.2; 525/333.6; 525/376; 525/377; 527/312
[58] Field of Search ............... 525/333.1, 333.2, 331.5, 525/330.5, 333.6; 527/312

[56] References Cited

U.S. PATENT DOCUMENTS 2,808,405  10/1957  Novak .................................. 536/32
3,301,848   1/1967  Halleck ............................... 106/162

FOREIGN PATENT DOCUMENTS 23854    2/1981  European Pat. Off. .
2728781 11/1982  Fed. Rep. of Germany .
2066460  7/1971  France .
2078435  4/1972  France .

OTHER PUBLICATIONS

European Search Report of French Application No. 83 10 773.
European Search Report of Application No. EP 80 40 1053.
Chemical Abstracts (1972), vol. 77, No. 18, "Polymeric Stabilizers of Aging", G. F. Bebikh et al., p. 21.
Boisson et al., Abstract to 11th Annual Meeting of the Society for Biomaterials, San Diego, California, 1985.
Okamoto et al., "Thrombin Inhibitors. 1. Ester Derivatives of N-(Arylsulfonyl)-L-Arginine, J. Med. Chem. 23:827 (1980).
Okamoto et al., "Thrombin Inhibitors 3. Carboxyl-Containing Amide Derivatives of $N^a$-Substituted L-Arginine, J. Med. Chem. 23:1293 (1980).

Primary Examiner—Christopher A. Henderson
Attorney, Agent, or Firm—Oblon, Fisher, Spivak, McClelland & Maier

[57] ABSTRACT

Product constituted by a polymer or a copolymer having in its chain substitutable groups to which are statistically fixed X and Y groups, in which X represents SO$_3$—R$^1$, with R$^1$ being a hydrogen atom or a physiologically acceptable metal, wherein the Y groups have the formula —SO$_2$—R$^2$, in which R$^2$ represents a radical derived from arginine or an arginine derivative, bonded by its amino function —NH— to the radical —SO$_2$—.

The invention also relates to a process for preparing such a product and to a process of the separation and purification of thrombin.

11 Claims, 10 Drawing Figures

FIG.10

PRODUCTS BASED ON POLYMERS OR COPOLYMERS SUBSTITUTED BY GROUPS HAVING SELECTIVE AFFINITY TOWARDS PRODUCTS INVOLVED IN BLOOD PLASMA COAGULATION AND PROCESS FOR PREPARING SAME

BACKGROUND OF THE INVENTION

1. Field of the Invention

The present invention relates to products based on polymers or copolymers substituted by groups able to give them a selective affinity with respect to products involved in the blood plasma coagulation process, such as thrombin and certain coagulation factors, such as VII and X factors. The invention also relates to a process for the preparation of products having these characteristics and the use of these products for the separation and purification of thrombin.

More specifically, the invention relates to products based on polymers or copolymers having in their chain substitutable groups, to which are statistically fixed groups X and Y, which give them special properties.

2. Description of the Prior Art

Polymers of this type, in which the groups X and Y have special anticoagulating properties have more particularly been described in French Pat. No. 2,461,724. In this patent, the anticoagulating property is obtained by fixing to the polymer, an amino acid derivative preferably having at least one free carboxyl function, such as glutamic acid. When the amino acid has several amino functions, it is necessary according to the aforementioned patent to block all the amino functions except one by a physiologically acceptable electroattractor group, such as benzyloxycarbonyl or tertiobutyloxycarbonyl, in order to obtain a satisfactory anticoagulating activity better than that of a polymer which is only sulphonated.

Although they have an anticoagulating activity, the products described in the aforementioned French Patent do not have a selective affinity for thrombin, because their effect on the blood plasma coagulation process is identical to that of heparin and consequently they act as a catalyst. Thus, with respect to thrombin, they do not have an affinity and selectivity of an adequate nature to permit their use as adsorbents in a thrombin separation and purification process.

In addition, molecules derived from L-arginine are known, which have an inhibiting activity to thrombin, as has been described by Okamoto et al, in the Journal of Medicinal Chemistry, 1980, Vol. 23, No. 8, pp. 827 to 836 and 1293 to 1299, said derivatives being in accordance with the following formula:

The influence of the radical $R^1$ and the radical $R^2$ on the activity of these products is investigated. However, these authors give no details of the possible affinity and selectivity of such products for thrombin.

SUMMARY OF THE INVENTION

The present invention describes products based on polymers or copolymers having a selective affinity for thrombin and which can consequently be used for separating and purifying thrombin with respect to other proteins.

DESCRIPTION OF THE INVENTION

The product of this invention is constituted by a polymer or a copolymer having in its chain substitutable groups, to which are statistically fixed groups X and Y, in which X represents $-SO_3-R^1$ with $R^1$ being a hydrogen atom or a physiologically acceptable metal. The formula of the Y groups is $-SO_2-R^2$ in which $R^2$ is a radical derived from arginine or an arginine derivative, bonded by its $-NH-$ amino function to the $-SO_2-$ radical.

Preferably, $R^2$ represents the radical of formula:

in which $R^3$ represents hydrogen or a $C_1$ to $C_4$ alkyl radical and $R^4$ represents hydrogen or the $NO_2$ radical.

According to a preferred embodiment of the process according to the invention, the Y groups represent:

Thus, such a product has a very high affinity and selectivity for thrombin, which makes it particularly interesting. However, according to the invention, it is also possible to use products in which $R^2$ represents radicals of formula:

-continued

In order to obtain good results, according to the invention it is preferable for the proportion of the Y groups to be approximately 10 to 20% compared with all the X and Y groups fixed to the polymer or copolymer chain.

According to the invention, the polymers and copolymers which can be used are materials having along their chain groups able to react with chlorosulphonic acid.

Examples of such polymers are polystyrene, cellulose polyesters, cellulose polyethers, polyvinyl acetate, polyvinyl chloride, polyisoprene and polybutadiene. It is also possible to use copolymers obtained from styrene, cellulose esters, cellulose ethers, vinyl acetate, vinyl chloride, isoprene and butadiene.

Preferably, according to the invention, the polymer is polystyrene.

The products according to the invention can either be products soluble in water and in biological fluids, or products which are insoluble in water and in biological fluids. In the latter case, the basic polymer or copolymer carrying the X and Y groups is a crosslinked copolymer or polymer, which makes it insoluble.

The invention also relates to a process for the preparation of products constituted by substituted polymers or copolymers as described hereinbefore.

This process comprises:

(a) chlorosulphonating a polymer or copolymer by reacting it with chlorosulphonic acid, and (b) converting the —SO$_2$Cl groups fixed in this way to the polymer or copolymer into —SO$_3$R$^1$ and —SO$_2$R$^2$ groups, with R$^2$ representing a radical derived from arginine or an arginine derivative, by reacting the chlorosulphonated copolymer or polymer with arginine or the arginine derivative in a basic medium.

When the polymer is polystyrene, the chlorosulphonation reaction corresponds to the following reaction diagram:

The starting polymer can be a cross-linked or non-crosslinked polymer. When use is made of a non-crosslinked polymer for preparing the soluble product, sulfonation takes place in an organic medium, which is advantageously constituted by a chlorinated solvent, e.g. dichloromethane and the thus obtained chlorosulphonated polymer is then precipitated in nitromethane before reacting it with the arginine or arginine derivative, this preferably taking place in a medium taking a water-dioxan mixture for acids and a medium containing dichloromethane for arginine ester derivatives.

However, when it is wished to obtain insoluble substituted polymers, the starting product is a crosslinked polymer or copolymer and the reaction is performed in a mixture containing a chlorinated solvent, such as dichloromethane, and nitromethane. The reaction with the amino acid then takes place in a medium containing the water-dioxan mixture. A chlorosulfonic acid excess is used for the chlorosulfonation reaction.

The reaction of the chlorosulfonated copolymer or polymer with the arginine or arginine derivative takes place in a medium containing a water-dioxan mixture. During this reaction, which takes place in accordance with the following diagram:

there is a release of hydrochloric acid which acidifies the medium and the pH-value of the reaction medium is kept substantially at 8 by adding soda, so that it is possible to follow the progress of the reaction. The reaction is ended when the pH remains constant. During this reaction, parasitic reactions can occur and in particular a partial hydrolysis of the chlorosulphonated polystyrene in accordance with the following reaction diagram:

Thus, the product obtained will simultaneously have —SO$_2$-arginine groups and —SO$_3$H groups and more generally —SO$_3$Na groups, because the reaction is performed in a basic medium in the presence of soda.

When the groups —R$^2$ represent an alkyl ester of arginine, the chlorosulphonated polymer or copolymer is reacted with a hydrochloride of said methyl ester which is introduced in solution in dichloromethane. This is followed by the addition of triethylamine in order to release the hydrochloride. The chlorosulphonated copolymer or polymer, preferably previously swollen by dichloromethane, is then introduced. The triethylamine quantity necessary for releasing the hydrochloride from the chlorosulphonated polymer or copolymer is then gradually added.

Following the reaction with the arginine or arginine derivative, the thus obtained modified crosslinked polymer or copolymer preferably undergoes a purification treatment in order to eliminate all the impurities liable to interact with the coagulation factors. Moreover, the product is preferably balanced at a physiological pH-value.

This purification treatment is generally carried out by performing several washing operations using a sodium chloride solution, followed by washing with distilled water, washing with sodium citrate, washing with the Michaelis buffer, rinsing with distilled water and drying in the oven. Following these operations, the products obtained are generally ground or milled in a planetary grinder or mill, in order to obtain finer particles, because they have proved to be more effective in absorbing the thrombin or other coagulation factors. Generally, this operation takes place in a planetary grinder, in order to obtain products with an average grain size between 2 and 100 μm, as a function of the grinding time.

The products obtained by the process according to the invention thus simultaneously comprise —SO$_3$R$^1$ groups and —SO$_2$R$^2$ groups and it is possible to vary the number of —SO$_2$— groups within a wide range, e.g. between 1 and 60% by controlling the progress of the reaction.

However, in order to obtain products having a good affinity with respect to thrombin, it is in some cases preferable to limit to values below 20%, the number of arginine groups or arginine derivatives fixed to the polymer or copolymer.

Thus, in the case of polystyrene having Y groups derived from arginine methyl ester, the best results are generally obtained when the number of fixed Y groups is 10 to 20% with respect to all the X and Y groups.

The products according to the invention in particular have a very good selectivity for thrombin. Thus, when the products are insoluble, they can selectively adsorb large quantities of thrombin and the thrombin can then be recovered by desorption with appropriate solutions, e.g. with a 1.5M sodium chlrride solution or hexadimethrine bromide (Polybrene). This is very interesting because it has been proved that the enzymatic activity of the thus recovered thrombin is maintained.

In the same way, the products according to the invention have a very high affinity for factors VII and X involved in the blood coagulation or clotting process and they thus have the property of being able to adsorb VIII C antibodies.

Thus, there are numerous applications for the products according to the invention. The products insoluble in water and biological fluids can be used for producing various objects, such as cardiovascular prostheses, catheters, suture threads, etc made from anticoagulating material. The products which are soluble in water and biological fluids can be used for preparing solutions having an anticoagulating action for pharmaceutical use.

However, one of the most interesting applications of the products according to the invention, when they are in the form of products insoluble in water and biological fluids, is the production of selective adsorbents with respect to thrombin.

The invention also relates to a process for the separation and purification of thrombin consisting of contacting an insoluble product constituted by a crosslinked polymer or copolymer having in its chain —SO$_3$—R$^1$ groups with R$^1$ representing hydrogen or a physiologically acceptable metal and —SO$_2$—R$^2$ groups with R$^2$ representing a radical from arginine or an arginine derivative bonded to —SO$_2$— by its —NH— amino function with a solution containing thrombin, separating the product which has adsorbed the thrombin from said solution and recovering the thrombin by desorption using a solution of sodium chloride or hexadimethrine bromide.

Preferably, the insoluble product used is crosslinked polystyrene having —SO$_3$Na groups and

BRIEF DESCRIPTION OF THE DRAWINGS

The invention is described in greater detail hereinafter relative to non-limitative embodiments and with reference to the attached drawings, wherein show.

EXAMPLES OF THE INVENTION

Example 1

This example illustrates the preparation of crosslinked polystyrene having SO$_2$Na groups and groups (a) Synthesis of the chlorosulphonated polystyrene 100 g of a crosslinked polystyrene powder with a grain size of 50 to 130 μm are placed in 800 ml of 1M NaOH, accompanied by gentle stirring at ambient temperature for 1 hour. The powder is filtered in vacuo, washed with distilled water and stirred gently again in 400 ml of 1M HCl for 1 hour. The powder is filtered in vacuo, washed with distilled water and then methanol and finally dried in vacuo at 40° C.

20 g of the thus washed polystyrene powder are taken and mixed with 160 ml of CH$_2$Cl$_2$ in a dry balloon flask and is then gently stirred for 1 hour. This is followed by the addition under the hood of 130 ml of nitromethane and 110 ml of HSO$_3$Cl, the complete mixture then being placed in an oil bath for 4 hours at 40° C. The powder is filtered in vacuo and the filtrate is gently deactivated with 50 ml of CH$_2$Cl$_2$ and alcohol. The powder is then washed by means of nitromethane, then CH$_2$Cl$_2$ and dioxan, followed by drying in vacuo at 40° C. In this way, 20 g of chlorosulphonated polystyrene powder are obtained.

(b) Fixing arginine monohydrochloride to chlorosulphonated polystyrene powder

In a 300 ml beaker, 20 g of arginine monohydrochloride are introduced in the presence of 150 ml of a mixture of water and dioxan containing 94 ml of water and 56 ml of dioxan. 2M NaOH soda is then added to completely solubilize the arginine. This is followed by the addition of 10 g of the previously obtained chlorosulphonated polystyrene powder and the pH-value is kept at 8 to 9 by adding soda. The reaction is ended when there is no variation to the pH-value. The powder is then filtered, washed abundantly with distilled water, then with a 0.5M NaOH soda solution and is then kept in water accompanied by gentle stirring overnight. The powder is then filtered washed with distilled water and dried in vacuo at 40° C. The same procedure is used for fixing nitroarginine (PNA).

(c) Characterization

The nitrogen, sulphur and chlorine contents of the product obtained are then determined by elementary analysis and the chlorine level is determined by argentimetric determination of the ions released by hydrolysis. The quantity of fixed arginine is also determined by carrying out an acid-base determination of the carboxyl functions, which makes it possible to calculate the percentages of unmodified styrene sites (W), sulphonates (X), arginine (Y) and the byproduct (Z) of the products obtained. The results are given in the following table 1.

Examples 2 to 7

These examples illustrate the preparation of polystyrene having —SO$_3$Na groups and

As in example 1, chlorosulphonated polystyrene is prepared and in each example use is made of 10 g of chlorosulphonated polystyrene.

Accompanied by stirring, 16.6 g (64 mmol) of arginine methyl ester hydrochloride are dissolved in 300 ml of CH$_2$Cl$_2$ in a dry balloon flask. This is followed by the addition to the mixture of 29 ml (200 mmol) of triethylamine in order to release the hydrochloride, as well as 10 g of chlorosulphonated polystyrene (42.6 meq of SO$_2$Sl). This is followed by the slow addition of 6 ml (43 mmol) of triethylamine and stirring of the mixture is maintained for 16 hours at 20° C. The polystyrene is then filtered in vacuo, followed by washing with dioxan and water and drying in vacuo at 40° C.

The products obtained undergo the same analyses as in example 1 and the results obtained also appear in table 1.

Example 8

This example illustrates the preparation of chlorosulphonated polystyrene having —SO$_3$Na groups and As in example 1, chlorosulphonated polystyrene with a 42.6 meq content of SO$_2$Cl groups is prepared. Use is made of 10 g of said chlorosulphonated polystyrene and it is modified by fixing the nitroarginine methyl ester using the same operating procedure as in examples 2 to 7, except that use is made of 17 g (64 mmol) of nitroarginine hydrochloride instead of arginine methylester hydrochloride. At the end of the operation, the product obtained undergoes the same analyses as in example 1 and the results obtained are also shown in table 1.

Example 9

In this example, the products obtained in examples 2 and 3 are treated, with a view to using them for inactivating thrombin. Firstly, the products obtained undergo a treatment to completely eliminate the impurities which might react with the blood proteins. To this end, two washing operations are firstly performed with 1.5M NaCl using 250 ml of NaCl for 4 g of polystyrene, whilst gently stirring the mixture for 2 hours. The modified polystyrene powder is then filtered, following by washing with distilled water and washing twice with 1 m trisodium citrate, accompanied by gentle stirring for 2 hours. The powder is then suspended for 2 hours in the Michaelis buffer at a pH of approximately 7.32. This is followed by filtering, abundant washing with distilled water and drying in the oven in vacuo. The powder is then ground for 3 hours in a planetary grinder and the average diameter of the particles obtained is measured using direct observation with the optical microscope and the Coultronix method based on the Brownian motion. Finally, the degree of swelling S of the powder in the Michaelis buffer is determined and corresponds to:

$$S \text{ (in \%)} = \frac{W - W_0}{W_0} \times 100$$

in which $W_0$ and $W$ respectively represent the weight of the dry powder and the weight of the hydrated powder in a Michaelis buffer. The results obtained are given in table 2.

TABLE 2

| Product | Average grain size (μm) | Degree of swelling (in %) |
|---|---|---|
| Ex. 2 | 66 (unground) | 2.50 |
| Ex. 2 | 1.6 (ground) | |
| Ex. 3 | 83 (unground) | 2.57 |

Example 10

The anticoagulating properties of the products according to the invention are tested in this example by carrying out the following tests:

(a) determining the coagulation time of the human plasma incubated with a solution containing crosslinked polystyrene particles modified according to the invention and after starting coagulation by adding thrombin;

(b) determining the coagulation time of the fibrinogen incubated with the same polymer solution;

(c) determining the control coagulation time of the human plasma by replacing the polystyrene suspension with a buffer solution;

(d) determining the control coagulation time of the fibrinogen replacing the polystyrene suspension by a buffer solution;

(e) determining the coagulation time of the fibrinogen or plasma in the presence of a polystyrene solution modified according to the invention, whilst starting coagulation by adding reptilase.

In this example, use is made of cross-linked polystyrene having —SO$_3$Na groups and (PAOM) obtained in example 2.

The other reagents used are as follows. The plasma deficient in platelets (PPP) is prepared from citrated human blood and is then stored in fractions at a temperature of −8° C. The samples are thawed and stored at 4° C. before the test. The human thrombin comes from the Centre National de transfusion Sanguine (CNTS), Paris and has a concentration of 1094 NIH U/mg. It is dissolved in a Michaelis buffer and stored at −80° C. It is kept at 4° C. before the test. The human fibrinogen also comes from CNTS in Paris and it is dissolved at a rate of 6 mg/ml in a 0.15M NaCl solution. It is kept at 37° C. during the test. The reptilase, supplied by the Stago Company, is diluted in distilled water and kept at 37° C. before use.

The crosslinked polystyrene samples containing arginine methyl ester groups are suspended in a Michaelis buffer and ultrasonically degassed before the test.

In order to determine the different coagulation times, 0.05 ml of a PAOM suspension or 0.05 ml of a buffer are incubated with 0.20 ml of human plasma deficient in platelets for 10 minutes at 27° C. This is followed by the addition of 0.05 ml of a thrombin solution (15 NIH U/ml) and the coagulation time is determined at 37° C. using a KCl coagulometer.

Tests are carried out under the same conditions using a 6 mg/ml fibrinogen solution instead of the platelet-deficient plasma. Coagulation tests are also carried out on PPP and on fibrinogen under the same conditions, but the thrombin is replaced by reptilase.

This is followed by coagulation tests on the platelet-deficient plasma and on the fibrinogen using 0.05 ml of buffer instead of 0.05 ml of polystyrene suspension and whilst adding 0.05 ml of thrombin at variable concentrations in order to plot calibration curves representing the coagulation time of the plasma or the fibrinogen, as a function of the free thrombin concentration.

On the basis of these results, it is possible to determine the thrombin level inactivated by polystyrene modified by arginine methyl ester (PAOM). Different tests are performed by varying the PAOM concentration of the suspension, so as to determine the inactivated thrombin level as a function of the PAOM concentration of the suspension.

Figure 1:
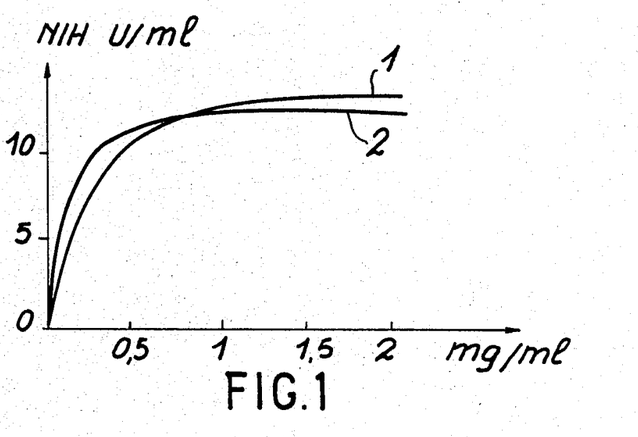
FIGS. 1 to 4 graphs illustrating the coagulation test results of a plasma deficient in platelets or fibrinogen and representing variations in the inactivated thrombin quantity as a function of the crosslinked polystyrene concentration modified according to the invention.

The results obtained are given in FIG. 1, which represents the inactivated thrombin level (in NIH U/ml) as a function of the polystyrene concentration of the suspension (in mg/ml). Curve 1 relates to tests carried out on platelet-deficient plasma and curve 2 relates to tests carried out on fibrinogen. In these tests, use is made of the PAOM of example 2 which has undergone grinding and has an average grain size of 1.6 μm.

Figure 2:
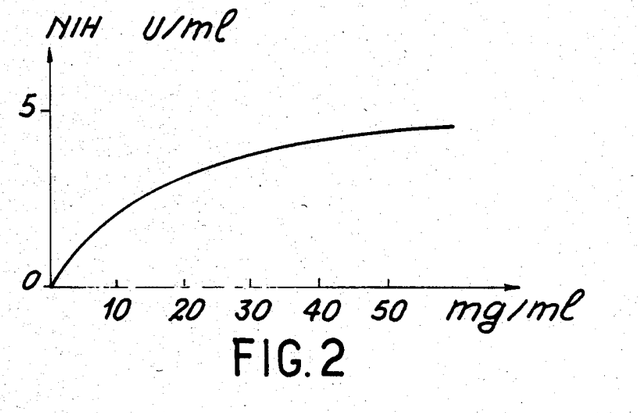

FIG. 2 illustrates the results obtained in coagulation tests performed on plasma when using PAOM, which has not undergone grinding and which therefore has an average grain size of 66±3 μm. FIG. 2 also shows variations in the inactivated thrombin level as a function of the polymer concentration of the suspension.

By comparing curve 1 of FIG. 1 and curve 1 of FIG. 2, it can be seen that the use of a PAOM powder with an average grain size of 1.6 μm makes it possible to have inactivated thrombin levels well above those obtained with PAOM with an average grain size of 66 μm. Thus, after grinding, the PAOM is able to inhibit large thrombin quantities, which is doubtless due to the larger proportion of accessible active sites on the surface of the grains.

On comparing the results obtained on the plasma and on the fibrinogen, (curves 1 and 2 of FIG. 1), it can be seen that the anticoagulating action of PAOM does not require the presence of a thrombin inhibitor, such as antithrombin III, which demonstrates that the PAOM does not have the same behaviour as heparin.

Finally, at the end of these tests, it was found that the coagulation times by means of reptilase remains normal in the presence of the PAOM suspension. It is possible to deduce therefrom that the anticoagulating effect of PAOM according to the invention is not due to a degradation of the fibrinogen.

Example 11

The same coagulation tests are performed using a polystyrene suspension modified with arginine (PA), obtained in example 1, or polystyrene modified by nitroarginine methyl ester (PNAOM) obtained in example 8. The results obtained are given in FIGS. 3 and 4, which represent the inactivated thrombin level, as a function of the PA or PNAOM concentration of the suspension.

Figure 3:
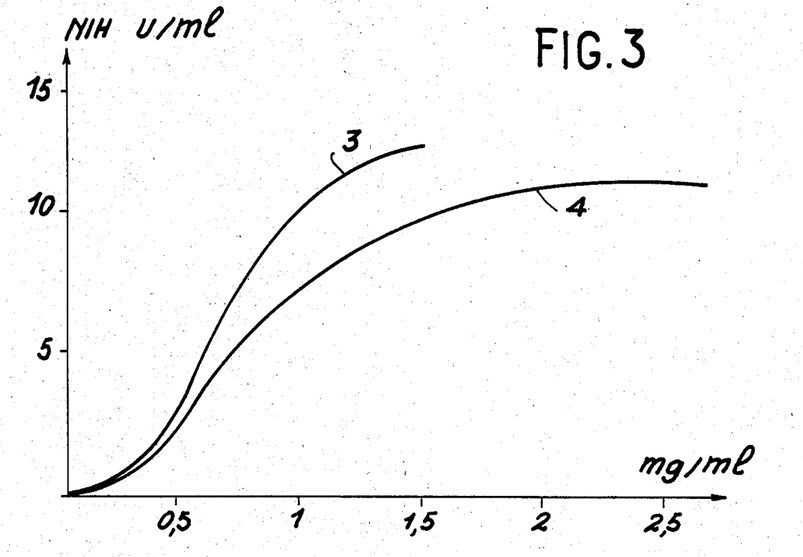
Figure 4:
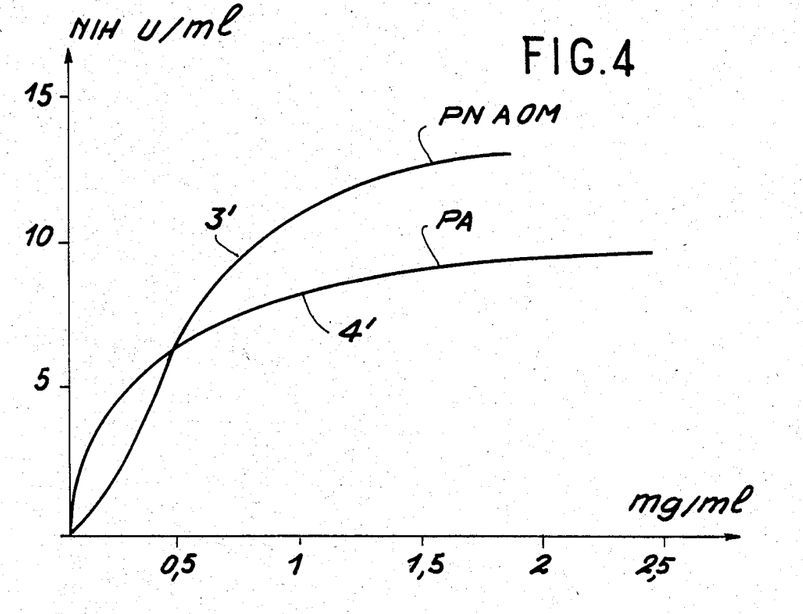

FIG. 3 relates to tests carried out on the plasma and FIG. 4 to tests carried out on fibrinogen. Curves 3 and 3' relate to PNAOM and curves 4 and 4' to PA.

Example 12

In this example, thrombin adsorption tests are carried out on the PA of example 1, the PAOM of example 2 and the PNAOM of example 8, whilst following the following operation procedure.

0.2 ml of a suspension of PA, PAOM or PNAOM or 0.2 ml of Michaelis buffer are suspended with 0.2 ml of thrombin at different concentrations and for different periods of time at 37° C. After decanting or settling, 0.1 ml of supernatant liquid is sampled and it is added to 0.2 ml of platelet-deficient plasma (PPP). The coagulation time is then measured and a calibration curve is used for determining on the basis of the results obtained in the tests, the level of thrombin remaining in the supernatant liquid. The adsorbed thrombin level corresponds to the difference between the thrombin quantity introduced and the thrombin quantity remaining in the supernatant liquid.

Figure 5:
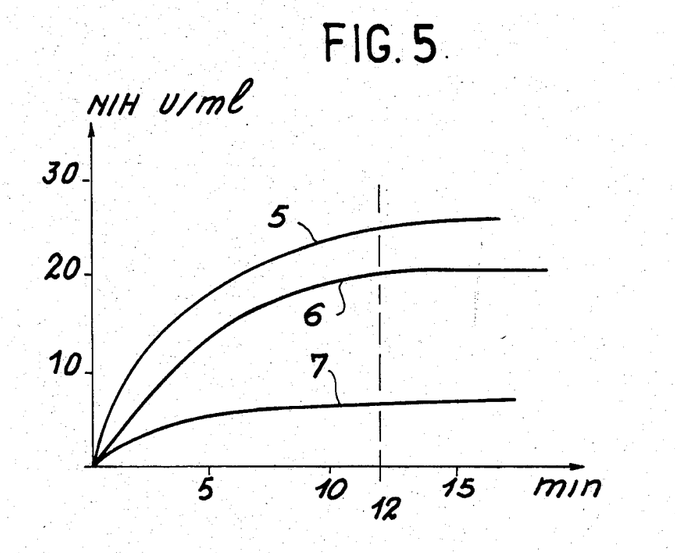
FIG. 5 a graph showing the variations of the inactivated thrombin level as a function of the incubation period.

The results obtained with the PAOM of example 2 are given in FIG. 5, which represents the adsorbed thrombin level (in U/ml) as a function of the incubation period (in min). Curve 5 relates to tests performed with a PAOM suspension with a concentration of 4.6 mg/ml and 0.2 ml of thrombin at 50 NIH U/ml. Curve 6 relates to the use of a suspension containing 15 mg/ml of PAOM and 0.2 ml of thrombin at 25 NIH U/ml. Curve 7 relates to tests performed with a suspension containing 7.5 ml/ml of PAOM and 0.2 ml of thrombin at 10 NIN U/ml.

The results obtained in FIG. 5 show that the adsorption of thrombin on the surface of PAOM particles increases with time, but that saturation is reached at the end of 12 minutes.

Figure 6:
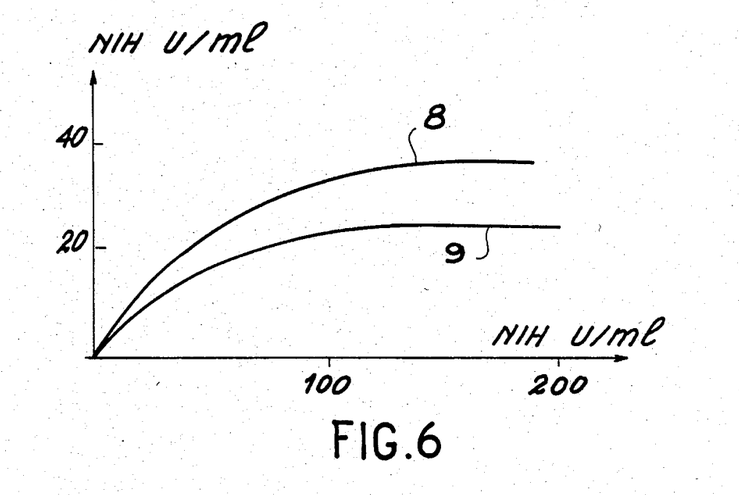
FIG. 6 the adsorbed thrombin level as a function of the initially introduced thrombin quantity.
Figure 7:
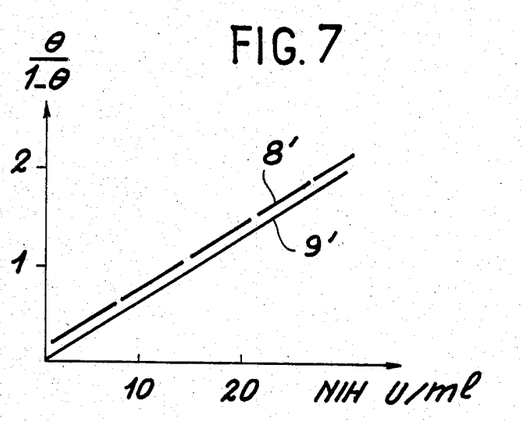
FIG. 7 variations in the ratio $\theta/(1-\theta)$ as a function of the thrombin concentration remaining in the medium.

FIG. 6 shows the adsorption isotherms of thrombin on the PAOM particles of example 2, whilst carrying out the tests under the same conditions as hereinbefore, but limiting the contacting time of the PAOM suspension and the thrombin to 12 minutes. Curve 8 illustrates the results obtained when using a PAOM suspension containing 7.5 mg/ml of PAOM and curve 9 illustrates the results obtained when the PAOM content of the suspension is 4.6 mg/ml. These curves represent variations of the adsorbed thrombin level as a function of the initial thrombin concentration (in NIH U/ml). Curve 9 corresponds to a PAOM content of 4.6 mg/ml, which initially has a gentle gradient and which reaches a plateau for an initial thrombin concentration of approximately 110 NIH U/ml. Thus, it is possible to conclude therefrom that the thrombin adsorption is limited to 27 NIH U/ml under the test conditions and that 1 mg of resin can absorb 5.9 NIH U/ml of thrombin. Bearing in mind the size of the PAOM particles, it can be assumed that the superficial thrombin concentration is $1.7 \pm 0.5$ $\mu g/cm^2$. It is thus possible to determine the ratio $\theta/(1-\theta)$ in which $\theta$ represents the thrombin-covered PAOM surface. FIG. 7 represents the variations of this ratio as a function of the free thrombin concentration in NIH U/ml. On the basis of these results, it is possible to determine the affinity constant between PAOM and thrombin and its value, which is independent of the grain size and of the PAOM concentration of the suspension is equal to $2.3 \pm 0.2 \ 10^6 \ 1 \ mol^{-1}$.

Example 13

In this example, adsorption tests are again performed following the operating procedure of example 12, but using polystyrene particles which have been modified by the arginine obtained in example 1 (PA) with a particle size of 2 to 70 μm and polystyrene particles modified by nitroarginine methyl ester (PNAOM) of example 8 having a diameter of 24 μm, as well as polystyrene particles modified by nitroarginine (PNA) of diameter 35 μm. The adsorbed thrombin level is determined as a function of the initial thrombin concentration added to the suspension (in NIH U/ml).

Figure 8:
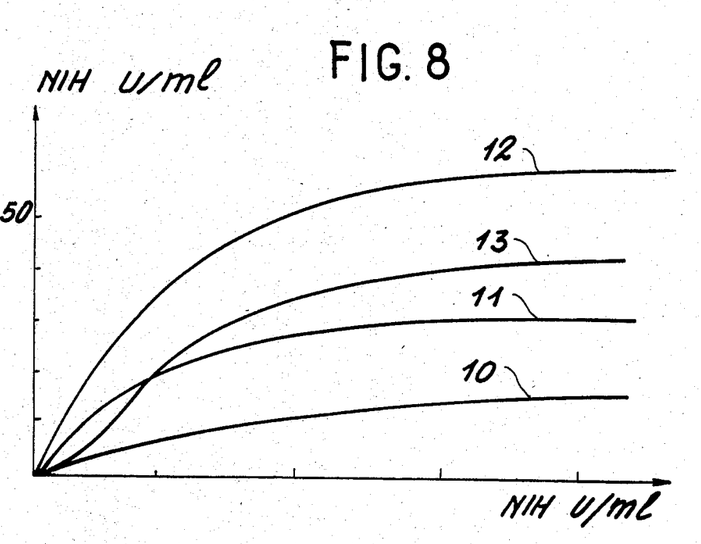
FIG. 8 variations in the adsorbed thrombin level as a function of the concentration of polystyrene crosslinked and modified according to the invention.

The results obtained are given in FIG. 8, which represents the variations of the adsorbed thrombin concentration as a function of the polymer concentration of the suspension. Curve 10 relates to PA, curve 11 to PNAOM and curve 12 to PNA. Curve 13 gives in a comparative form, the results obtained with PAOM particles with a grain size of 66 μm.

Example 14

In this example, contacting takes place in the presence or absence of a suspension of the PAOM particles of example 2 of thrombin and antithrombin III, which is a thrombin inhibitor and incubation is allowed to take at 37° C. for variable periods. This is followed by the measurement of the thrombin quantity remaining in the supernatant liquid. The results obtained are given in FIGS. 9 and 10 which represent the deactivated thrombin percentage (in NIH U/min), as a function of time (in minutes).

Figure 9:
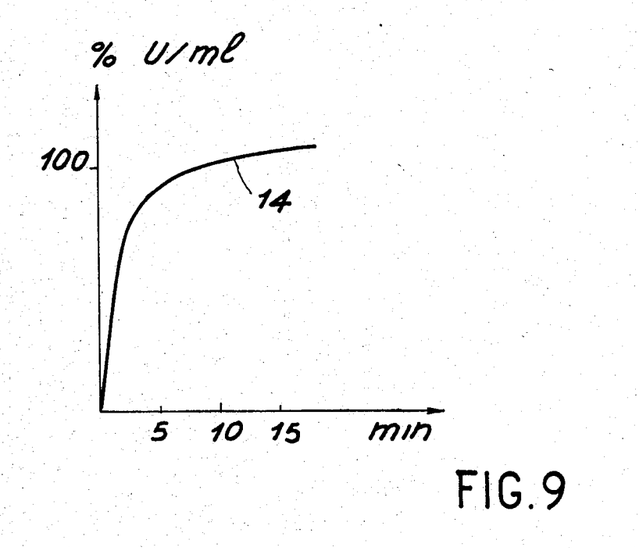
FIGS. 9 and 10 the results obtained in tests performed in the presence of antithrombin III and representing variations in the adsorbed thrombin percentage as a function of the incubation time.
Figure 10:
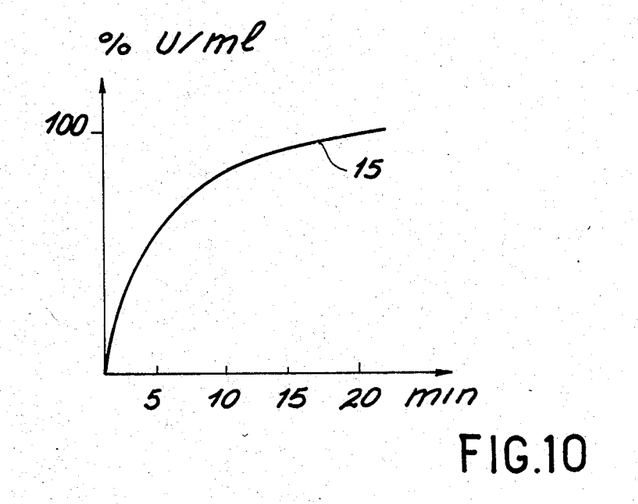

In FIG. 9, curve 14 represents the results obtained in the presence or absence of PAOM, when the antithrombin quantity corresponds to twice the thrombin quantity. In FIG. 10, curve 15 relates to the results obtained in the presence or absence of PAOM, when the antithrombin quantity is 3 times the thrombin quantity.

Thus, it can be seen that the presence of PAOM has no influence on the inhibition of thrombin by antithrombin III and that it does not act as a catalyst in the coagulation process.

TABLE 1

| Ex. | Resin Weight obtained (g) | Acid-base determination (meq/g) | Microanalysis N meq/g | (1) W (%) | (2) X (%) | (3) Y (%) | (4) Z (%) | Swelling level |
|---|---|---|---|---|---|---|---|---|
| 1 | PA1 | 14.86 | 1.19 | 1.69 | 16 | 20.9 | 55 | 2 | — |
| 2 | PAOM1 | 12.15 | 0.87 | 0.85–0.87 | 16 | 63 | 19 | 2 | 2.50 |
| 3 | PAOM2 | 5.66 | 0.96 | 0.96–0.99 | 16 | 60 | 22 | 1 | — |
| 4 | PAOM4 | 5.87 | 0.86 | 0.85–0.90 | 16 | 63 | 19 | 1 | — |
| 5 | PAOM5 | 11.44 | — | 0.154–0.2 | 16 | 79 | 3.0 | | — |
| 6 | PAOM6 | 9.03 | 0.89 | | 16 | 68 | 8.3 | | 2.46 |
| 7 | PAOM7 | 13.55 | 0.59–0.52 | 0.35 | 27 | 66 | 6.76 | | 3.00 |
| 8 | PNAOM1 | 4.13 | 1.00 | 1.10 | 35 | 40 | 24 | | — |

(1) W = ... —CH$_2$—CH— ...

(2) X = ... —CH$_2$—CH— ...

(3) Y = ... —CH$_2$—CH— ...

(4) Z = ... —CH$_2$—CH— ...

wherein:

$R^3$ is hydrogen or $C_1$–$C_4$ alkyl, and
$R^4$ is hydrogen or $NO_2$.

2. The product of claim 1, wherein $R^2$ is:

3. The product of claim 1, wherein $R^2$ is:

What is claimed is:

1. A product constituted by a polymer having in its chain substitutable groups to which are statistically fixed X and Y groups, wherein:
   X is $SO_3$—$R^1$, wherein $R^1$ is hydrogen or a physiologically acceptable metal, and
   Y is —$SO_2$—$R^2$, wherein $R^2$ has the formula:

4. The product of claim 1, wherein R² is:

5. The product of claim 1, wherein R² is:

6. The product of claim 1, wherein the polymer is selected from the group consisting of:
   polystyrene,
   cellulose polyesters,
   cellulose polyethers,
   polyvinyl acetate,
   polyvinyl chloride,
   polyisoprene, and
   polybutadiene.
7. The product of claim 6, wherein the polymer is polystyrene.
8. The product of claim 1, wherein the polymer is a copolymer comprising
   styrene,
   cellulose ester,
   cellulose ether,
   vinyl acetate,
   vinyl chloride,
   isoprene, or
   butadiene.
9. A water-insoluble product formed of a crosslinked polymer of claim 1.
10. The product of claim 1, wherein the said polymer is a copolymer.
11. The product of claim 9, wherein the said polymer is a copolymer.

* * * * *